United States Patent [19]

Piergiorgio et al.

[11] Patent Number: 4,880,623

[45] Date of Patent: Nov. 14, 1989

[54] PROCESS FOR THE PREPARATION OF SOLID NIFEDIPINE FORMULATIONS OF HIGH BIOAVAILABILITY AND WITH SUSTAINED EFFECT, AND FORMULATIONS THUS OBTAINED

[75] Inventors: Rossi Piergiorgio, Milan; Calanchi Massimo, Monza, both of Italy

[73] Assignee: Eurand Italia S.p.A., Milan, Italy

[21] Appl. No.: 918,382

[22] Filed: Oct. 14, 1986

[30] Foreign Application Priority Data

Oct. 15, 1985 [IT] Italy ................................ 22494 A/85

[51] Int. Cl.$^4$ .......................... A61K 9/20; A61K 9/22; A61K 31/74
[52] U.S. Cl. ..................................... 424/78; 424/465; 424/468; 424/469; 424/470; 424/489
[58] Field of Search ................. 424/78, 465, 468, 469, 424/470, 489

[56] References Cited

U.S. PATENT DOCUMENTS

| | | | |
|---|---|---|---|
| 3,089,824 | 5/1963 | Wurster | 424/489 |
| 3,920,809 | 11/1975 | Thakkar | 424/80 |
| 3,988,439 | 10/1976 | Thakkar | 424/78 |
| 4,151,273 | 4/1979 | Riegelman et al. | 424/78 |
| 4,311,694 | 1/1982 | Krueger et al. | 514/537 |
| 4,412,986 | 11/1983 | Kawata et al. | 514/781 |
| 4,562,069 | 12/1985 | Hegsy et al. | 424/400 X |

FOREIGN PATENT DOCUMENTS

| | | |
|---|---|---|
| 1180277 | 1/1985 | Canada . |
| 0047899 | 3/1982 | European Pat. Off. . |
| 55-129221 | 10/1980 | Japan ...................... 424/497 |
| 86/01717 | 3/1986 | PCT Int'l Appl. ................. 424/462 |
| 1456618 | 11/1976 | United Kingdom . |
| 2139892 | 11/1984 | United Kingdom . |

OTHER PUBLICATIONS

I. Sugitomo et al., Article, Drug Development and Industrial Pharmacy, 6(2), pp. 137–160, (1980).
I. Sugitomo et al., Article, Chem. Pharm. Bull. 29(6), pp. 1715–1723, (1981).

*Primary Examiner*—Shep K. Rose
*Attorney, Agent, or Firm*—Gordon W. Hueschen

[57] ABSTRACT

The object of the present invention is a process which permits the increase of the bioavailability in the solid formulations of nifedipine and its derivatives. In consists in dissolving the active substance together with a polyethylene glycol, in a common solvent, then absorbing this solution on a micronized, inert excipient, soluble in the gastrointestinal juices, and finally, co-precipitating the active substance and the polyethylene glycol by evaporating the solvent.

The very large surface of the excipient on which the solution is absorbed, and the presence of polyethylene glycol, which facilitate the homogeneous distribution of the solution on this surface, permit the active substance to precipitate and become very fine particles.

The same results may be also obtained by blending homogeneously the micronized inert excipient with micronized nifedipine, and causing the mixture to be absorbed on a solution of polyethylene glycol, which by subsequent solvent evaporation, precipitates in fine particles that are homogeneously dispersed and in intimate contact with the active substance.

Forms of solid dosage prepared with the mixture thus obtained, have shown a bioavailability higher than similar formulations already on the market.

13 Claims, 2 Drawing Sheets

FIG. 2

PROCESS FOR THE PREPARATION OF SOLID NIFEDIPINE FORMULATIONS OF HIGH BIOAVAILABILITY AND WITH SUSTAINED EFFECT, AND FORMULATIONS THUS OBTAINED

The present invention relates to a process allowing to increase the bioavailability of Nifedipine and its derivatives with respect to other solid oral forms. This process consists in coprecipitating Nifedipine and polyethylene glycol from a solution, into a very high surface obtained by means of the micronization of an inert excipient soluble in the gastrointestinal juices or in precipitating polyethylene glycol on a homogenous mixture of Nifedipine and an inert excipient, both being micronized.

Due to the low solubility and the high sensitivity to light, Nifedipine presents notable drawbacks in the preparation of stable and bioavailable forms. Nowadays nifedipine is mostly administered in a suspensions of liquid excipients, consisting essentially of propylene and polyethylene glycols, in the forms of soft gelatine capsules. Instead, the solid oral forms, tablets, sugar-coated pills, hard gelatine capsules, are absorbed very slowly and consequently are used as retard compositions. However, these are characterized by a bioavailability distinctly inferior to that of the rapid formulations: generally between 40 and 80%. The scarse absorption and the low bioavailability of crystalline nifedipine administered orally is made evident in the articles of I. Sugitomo et al. published on Drug Development and Industrial Pharmacy, 6 (2), 137–160 (1980), and Chem. Pharm. Bull. 29 (6), 1715–1723 (1981).

In order to increase the bioavailabiity of nifedipine, different techniques have been tried, namely, for example, the transformation of the crystals into fine powder, the transformation from the crystalline to the amorphus form, the formation of clathrates or compounds of inclusion with betacyclodextrines, the formation of solid solutions with polyethylene glycols, the formation of co-precipitates with polyvinylpyrrolidone.

U.K. patent specification GB-2139892 discloses the preparation of tablets containing nifedipine partially in the form of ground crystals, so as to reduce the dimension between 1 and 10 microns, partially in the form of co-precipitate with polyvinylpirrolidone, methylcellulose, hydroxypropylmethylcellulose or hydroxypropylcellulose.

In Canadian patent specification CA-1180277, the improvement of the bioavailability of nifedipine is obtained by grinding the active substance so as to obtain a specific surface between 0.5 and 6 $m^2/g$, and mixing with excipients suitable for the preparation of the desired solid active-substance forms, namely, capsules, tablets, pills, sugar-coated pills or suppositories.

In U.K. patent specification GB-1456618, the aim is achieved by making a solution of nifedipine in polyethylene glycol of a molecular weight of 200–400 in the presence of a surfactant, and absorbing said solution on a sufficient quantity of one or more inert excipients, soluble or insoluble in the gastrointestinal juices, by simply transforming the product into a powder and being able to make tablets out of it. That is, the known property of the polyethylene glycols in giving solid solutions is exploited.

In German patent specification DE-2822882, cases are claimed wherein nifedipine is simply mixed with excipients such as polyvinylpyrrolidone, methylcellulose, hydroxypropylmethylcellulose, hydroxypropylcellulose, aminoacids, and others, alone or in the presence of surfactants and/or calcium lactate and inert excipients, and cases are claimed wherein nifedipine is co-precipitated on inert excipients from solutions with polyvinylpyrrolidone, with the other substances mentioned hereinbefore, alone or in the presence of surfactants and/or calcium lactate.

Also the process, subject of the present invention, relates to the preparation of solid forms of dosage of nifedipine or its derivatives, but it differs substantially from those previously cited. According to the present invention, in fact, a solution of nifedipine and polyethylene glycol of high molecular weight is made in a common solvent (or mixture of solvents) and the solution is dispersed on a micronized inert excipient which is soluble in the gastrointestinal juices.

The surfactant property of the polyethylene glicol of high molecular weight is therefore exploited so as to be able to "wet" the microparticles of the inert excipient with the solution, and spread it over all of the very high surface available so that, when the solvent evaporates, the nifedipine crystals which precipitate are tiny and remain as such due to the impossibility of swelling or aggregation between each other. It was also noted that it is possible to micronize Nifedipine, mixing it with the micronized inert excipient and then "wet" such a mixture with a polyethylene glycol solution. When the solvent evaporates, polyethylene glycol precipitates in very fine particles and in intimate contact with the Nifedipine particles. In both cases one obtains a granulate of Nifedipine and polyethylene glycol finely and homogeneously dispersed in the micronized inert excipient, thus having the same characteristics. It is important, moreover, that the inert excipient is easily soluble in the gastrointestinal juices so as to leave the nifedipine microcrystals free after swallowing.

The obtained granulate is finall mixed with the excipients suitable to the manufacture of the desired solid forms of dosage: preferably tablets, but also sugar-coated pills, lozenges and suppositories. Testing the bioavailability, it was surprisingly found that these tablets have the characteristics of a retard product and have a bioavailability equivalent to 100% of the oral forms on the market, wherein the active substance is in liquid suspension in soft gelatine capsules.

In the process specified in the present invention, polyethylene glycols with a molecular weight exceeding 2000, and preferably between 5000 and 6000, are used. The ratio between active substance and polyethylene glycol may vary in the interval between 20:80 and 80:20, and preferably 40:60 and 60:40.

Nifedipine and polyethylene glycol may be dissolved in a common solvent and successively this is evaporated to obtain the co-precipitate. Preferably, however, the solution is mixed, for example in a kneader, with a micronized inert excipient which is very soluble in the gastrointestinal juices, obtaining a granulate which is successively dried. In this phase, the co-precipitation of the active substance with the polyethylene glycol in intimate mixture with the inert excipient, is obtained. As already mentioned, alternatively one may add in the kneader a polyethylene glycol solution to a homogeneous mixture of Nifedipine and inert excipient, where both Nifedipine and excipient are micronized. Illustrative but non-limiting examples of the said micronized inert excipients are cited: sucrose, lactose, glucose, fructose, levulose, mannitol, sorbitol, glycocoll, xylitol, pentaerythrite, maltodextrine. The ratio between co-precipitate and inert excipient may vary in a very broad range, but, for technical-economical reasons, that preferred is between 1:20 and 1:4.

The granulate of active substance, polyethylene glycol and micronized inert excipient may be used directly for the preparation of tablets, preferably adding a lubricant agent.

It was also found that a further prolongation of the retardant effect can be obtained if substances which, when in contact with the gastrointestinal juices, swell again and successively dissolve themselves slowly such as, for instance, illustrative and non-limiting examples: hydroxypropylmethylcellulose, methylcellulose, hydroxypropylcellulose, carboxyvinyl polymers, xanthan gum, in quantities variable between 5% and 50% of the tablet weight and preferably between 10 and 30%, are added to the granulate prepared in the manners hereinbefore specified.

For the first time, the prolongation of the retardant effect admits a single daily administration, without reducing the bioavailability and therefore the efficiency of the active substance; in such a way, a greater compliance on the part of the patient is also obtained, which is an important factor in long-term therapies.

BRIEF DESCRIPTION OF THE DRAWINGS

Referring now to the drawings.

The following examples serve to better illustrate the present invention:

EXAMPLE 1

Three solutions having the composition illustrated in the following table:

| Components | Solution I g | Solution II g | Solution III g |
|---|---|---|---|
| Nifedipine | 110 | 100 | 90 |
| Polyethylene glycol (PEG 6000) | 110 | 100 | 90 |
| Acetone | 1010 | 920 | 830 |
| Deionized water | 190 | 170 | 150 | are prepared in the manner which is now specified:

Nifedipine is dissolved in acetone and PEG in water, using a suitable vessel equipped with stirrer.

The nifedipine acetonic solution and the aqueous PEG 6000 solution are then mixed in such a way so as to obtain the solutions indicated in the table. 3.9 kg of micronized lactose (90% inferior to 15 microns) are placed in a kneader with horizontal blades, to which 1.42 kg of solution I is added.

When the solution is homogeneously distributed, the mixture is transferred to a stove with forced air circulation where it is dessicated at 45° C. for 2 hours. It is granulated with an oscillating granulator provided with a inox ASTM No. 8 stainless steel metal wire mesh and dessication is completed.

The evaporation of the solvent causes the co-precipitation of the active substance and polyethylene glycol in fine form and homogeneously dispersed in the inert excipient.

The granulate thus obtained is ground so as to be able to proceed with the subsequent application of the active substance and polyethylene glycol solution.

Afterwards, the operations specified hereinbefore are repeated with solution II and then with solution III. After the last blending, the dried product is granulated through a inox ASTM No. 25 stainless steel wire mesh (openings of the mesh 0.71 mm).

The tablets are then prepared. For this purpose, 4.5 kg of granulate and 75 g of magnesium stearate are mixed for 15 min. in a cubic mixer.

A chromed punch with a capsular shape having a 15 mm length, a 6 mm width and a 5 mm bending radius, is used for the preparation of the tablets. Tablets having the following characteristics are obtained:

Nifedipine content: 20 mg
Theoretical weight: 305 mg
Hardness (determined with Erweka TBH 28 apparatus): 8–10 kg
Friability (measured with Roche friabilometer, by rotating 10 tablets for 4 min. and determining the loss of weight): inferior to 1%

EXAMPLE 2

Two solutions are prepared, having the compositions illustrated in the following table:

| Composition | Solution I | Solution II |
|---|---|---|
| Nifedipine | 220 g | 180 g |
| PEG 6000 | 220 g | 180 g |
| Methylene chloride | 3170 g | 2650 g | operating with the following method:

Nifedipine and methylene chloride are placed in a suitable vessel equipped with stirrer, and stirred until complete dissolution. Polyethylene glycol is added and stirred until complete dissolution.

5.2 kg of micronized mannitol is placed in a kneader and mixed with 3.610 kg of solution added by pouring thinly in about 2 min. When adding of the solution is terminated, mixing continues for 4–5 min.

During the latter operation, it is suitable to operate with a strong suction through the kneader lid to facilitate the evaporation of the methylene chloride.

The mixture is distributed on the grid of a stove, in a thin layer, and is dried with a single circulation of air at room temperature for about 2 hours or, anyway, until the almost total elimination of the methylene chloride.

Then granulation is done with an oscillating granulator provided with a inox ASTM No. 8 stainless steel mesh. The granulate is again distributed on the same grid and is dried with air circulation at 45° C. for over 2–3 hours.

After having ground the granulate, the operations are repeated using solution II operating with the same method.

After the last blending, the dried granulate must be granulated with the oscillating granulator provided with inox steel ASTM No. 25 wire mesh (opening 0.71 mm).

In a cubic mixer
60 kg of granulate
1 kg of stearate magnesium
8 kg of hydroxypropylmethylcellulosa (Methocel E 4 M)

are placed and mixed for 15 min.

A chromed capsule-shaped punch having 17.5 mm length, 7 mm width and 7 mm bending radius is used for the preparation of the tablets. Tablets having the following characteristics are thus obtained:
Nifedipine content: 40 mg
theoretic weight: 690 mg
hardness (determined as specified in example 1): 8–10
friability (determined as specified in example 1): inferior to 1%

EXAMPLE 3

In a suitable vessel equipped with stirrer 1100 g of deionized water are charged with 300 g PEG are dissolved in said water under agitation.

In a cube mixer 3900 g of micronized lactose (90% smaller than 4 microns) and 300 g of micronized nifedipine (with a total surface higher than 6 m²/g) are intimately mixed.

Such a mixture is charged in a kneader with horizontal blades and is wetted with the PEG aqueous solution.

When the solution is homogeneously distributed, the mixture is transferred to a stove with forced air circulation where it is dried for 2 hours at 45° C.

Granulation is effected with an oscillating granulator provided with a inox ASTM No. 8 stainless steel metal wire mesh and dessication is completed.

Tablets are then prepared as described in Example 1.

EXAMPLE 4

In a cube mixer 5.2 kg of micronized mannitol and 400 g of micronized nifedipine (with a total surface higher than 6 m²/g) are intimately mixed.

The mixture is charged in a kneader with horizontal blades and is wetted with a solution of 400 g PEG dissolved in 5820 g of methylene chloride. When the addition of the solution is terminated, mixing is continued for 4–5 minutes. During the latter operation it is suitable to operate with a strong suction through the kneader lid to facilitate the evaporation of methylene chloride.

The mixture is distributed on the grid of a stove, in a thin layer, and is dried with a single circulation of air at room temperature for about 2 hours or anyway until the almost total elimination of methylene chloride.

The dry granulate is granulated with an oscillating granulator provided with a inox ASTM No. 8 stainless steel mesh (wire mesh 0.71 mm). Tablets are then prepared as described in Example 2.

EXAMPLE 5

The tablets prepared according to the specifications in the examples 1 and 2 are analysed according to the method specified in the American Pharmacopaea (USP, XX ed., pag. 1243 and following, Apparatus 2, at a temperature of 37° C. and 125 r.p.m.

A tablet, having a dosage of 20 or 40 mg of active principle, is placed in 500 ml of acetic acid 5N, at a temperature of 37° C., oscillating the blade at 125 r.p.m.

Samples are withdrawn after 15, 30, 45, 60, 75 minutes for the 20 mg tablets and after 1, 2, 4, 6, 8, 10 hours for the 40 mg tablets and the quantity of nifedipine passed in solution is determined with a spectrophotometric method. The following percentage values of active substance released by the tablets are found:

| % of Nifedipine released after | | | | | |
|---|---|---|---|---|---|
| | 15 min. | 30 min. | 45 min. | 60 min. | 75 min. |
| Example 1 | 24 | 55 | 78 | 95 | 96 |
| Example 3 | 26 | 58 | 81 | 96 | 98 |
| | 1 hour | 2 hours | 4 hours | 6 hours | 8 hours | 10 hours |
| Example 2 | 10 | 20 | 42 | 62 | 81 | 100 |
| Example 4 | 13 | 23 | 49 | 64 | 82 | 100 |

EXAMPLE 6

The formulation in 20 mg tablets underwent a bioavailability test on six adult subjects, healthy and of both sexes, in comparison with a conventional rapid release preparation and one with substained release, both on the market.

The experimental products were labelled as follows:
"A"=Adalat (Bayer), 10 mg capsule (conventional product for comparison)
"B"=Adalat AR (Bayer), 20 mg tablets (sustained release product for comparison)
"C"=Nifedipine Example 1, 20 mg tablets The product "A" was administered in two successive doses of 10 mg each at zero time and at the sixth hour; the blood withdrawals for the determination of the blood plasmatic levels were effected after 1, 2, 3, 4, 5, 6, 7, 8, 9, 12, 14, 16, and 24 hours after swallowing of the first dose.

For the two preparations "B" and "C", instead, a single dose of 20 mg was administered and the blood withdrawals were done after 1, 2, 3, 4, 6, 9, 12 and 24 hours.

Figure 1:
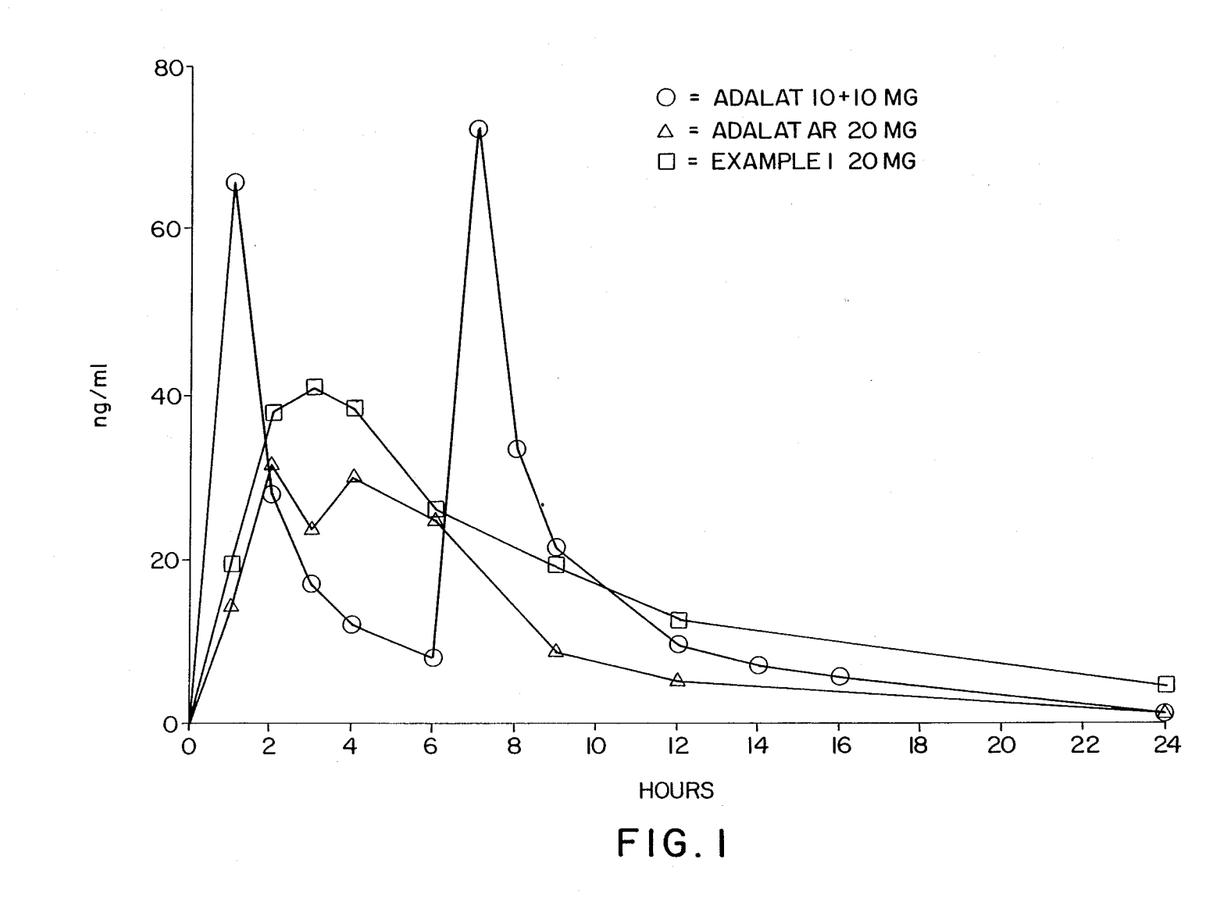
FIG. 1 is a graph illustrating bioavailability of a product of the invention as compared with two (2) commercially-available products of a similar nature.

The average curves of the plasmatic levels obtained, are reported in the table 1 and graphically illustrated in FIG. 1.

The maximum concentrations ($C_{max}$), the relative appearance times ($T_{max}$) and the areas under the concentration-time curve (AUC) from zero to infinity, were calculated from the average curves. These were obtained from the total of the area comprised between zero and the last level ($C_n$), calculated with the trapeze method, plus the $C_n/K_{el}$ portion, where $C_n$ represents the last level and $K_{el}$ is the elimination constant (x)(=0.185) of the conventional product.

As an indication of the sustained release characteristics of the preparations, the average residence times of nifedipine in the plasma were calculated (mean residence time =MRT) according to the formula $$MRT = \frac{AUMCoo}{AUCoo}$$

Wherein AUMCoo is the area under the first moment of the curve and AUCoo is the coventional area under the curve, both from zero to infinity.

The HVD (half value duration), that is the residence time of nifedipine in the plasma equal to half of the peak value, was calculated with graphic method.

The results obtained from the test prove that the preparation "B" (Adalat AR) shows an average peak value of 32 ng/ml after two hours from the administration of the 20 mg dose, whilst the conventional preparation "A" (Adalat) induces a peak value of 65.4 ng/ml as soon as one hour after swallowing of a 10 mg dose. The preparation "C" (Exemple 1) has a maximum concentration of 40.9 ng/ml after three hours from the administration of the 20 mg dose.

12 hours after the administration of the dose, the average levels of Adalat (6 hours after the second dose) and Adalat AR, respectively fall to 9.5 and to 5.1 ng/ml, whereas the average concentration is maintained at 12.6 ng/ml due to nifedipine in Example 1. A similar observation is made for the levels of the 24th hour, corresponding for "A", "B and "C", in order, to 0.95, 1.5 and 4.5 ng/ml (see Table 1 and FIG. 1).

(x) The $K_{el}$ of the conventional product was calculated according to a pharmacokinetic model with two compartments for extravascular administration (triexponential equation).

The calculation of the area under the curve (AUC) gave a confirmation of the good bioavailability of the preparation "C" with respect to the two comparison forms: the preparation "A" presents an AUC of 363.5 ng/mlxh while such value for preparation "B" is equal to 261.7 ng/mlxh (72% with respect to the previous), and rises to 423.3 ng/mlxh for the preparation "C", which corresponds to 116.5% with respect to the conventional product "A" and to 162% with respect to the sustained release product "B" (See Table 2).

The evaluation of the retard characteristics, based on a comparison of the parameters MRT and HVD, indicates more satisfying results proved by preparation "C". The latter's curve maintains significant average values higher than the previous products: in fact, the average value of the MRT is, for the specification "C", equal to 9.1 hours as opposed to the 7.1 of the similar sustained release product "B". The conventional product presents a MRT of only 4.4 hours, that is, about twice as little as that of product "C".

Also the HVD is 1.4 hours for the conventional product "A", rising to 6.6 hours for the sustained release product "B" and to 7.2 hours for the sustained release product "C" in Example 1 (see Table 3). Therefore, in parity of dosage, the product "C" also combines a good retard effect with a satisfactory bioavailability, equal to over one and a half times that of the similar Adalat AR product on the market.

TABLE 3-continued

PARAMETERS[a] INDICATING THE SUSTAINED RELEASE CHARACTERISTICS OF TEST PREPARATIONS

| preparation | MRT (h) | HV (ng/ml) | HVD (h) |
|---|---|---|---|
| "C" | 9.1 | 20.5 | 7.2 |

[a] MRT = mean residence time
HV = half value
HVD = half value duration

EXAMPLE 7

The formulation in 40 mg tablets (Example 2) underwent a bioavailability test on six healthy adults of both sexes, in comparison with a sustained release product already on the market.

The experimental products were labelled as follows:
"A" = Adalat AR (Bayer), 20 mg tablets
"B" = Nifedipine of Example 2, 40 mg tablets The product "A" was administered in two successive doses of 20 mg, the first at zero time and the second after 12 hours: the blood withdrawals were effected after 1, 2, 4, 6, 9, 12, 14, 16, 18, 22 and 24 hours from the assumption of the first dose.

Preparation "B", instead, was administered in a single dose of 40 mg and the blood withdrawals were effected after 1, 2, 4, 6, 9, 12, 16 and 24 hours.

Figure 2:
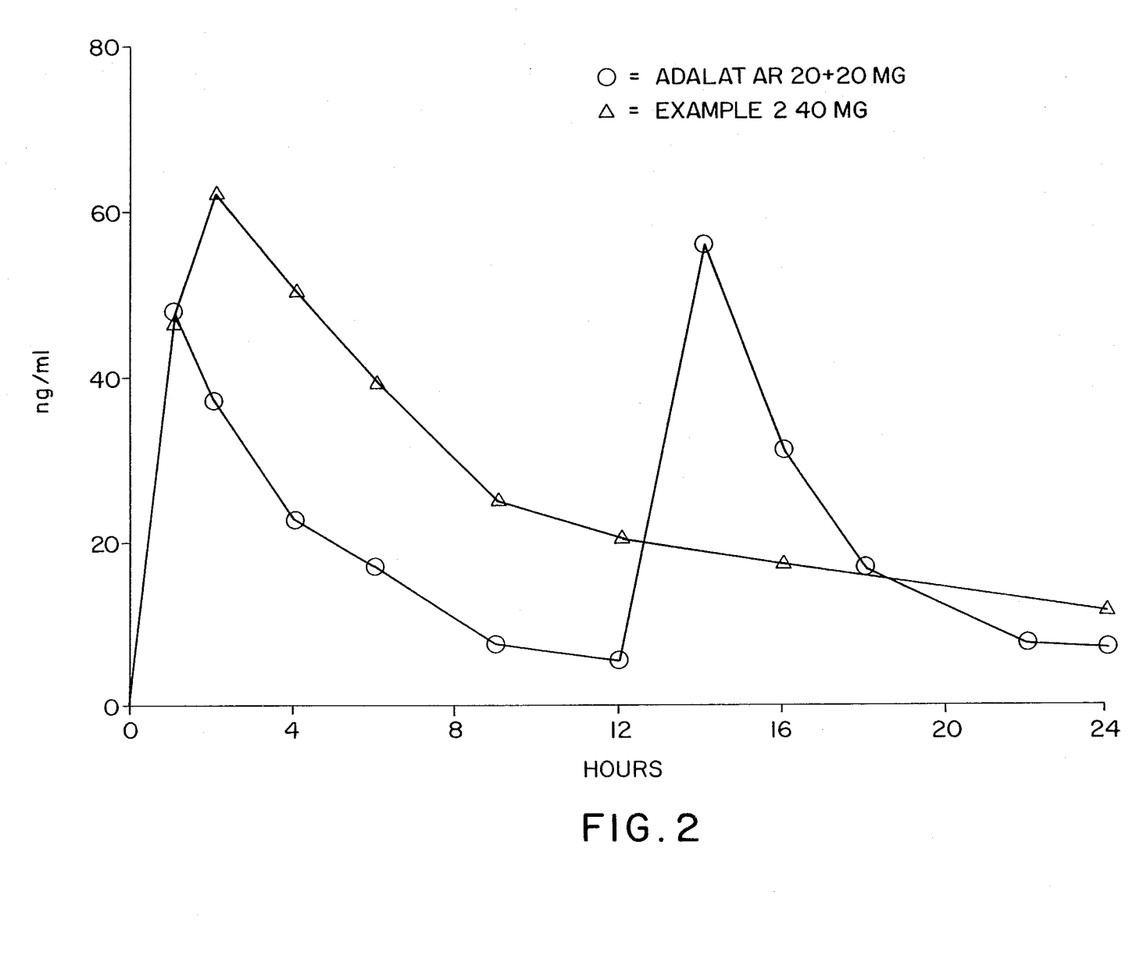
FIG. 2 is another graph illustrating bioavailability of another product of the invention as compared with a similar commercially-available product, both FIGS being discussed further hereinafter.

The obtained average curves of the plasmatic levels are reported in Table 1A and illustrated in FIG. 2. From these, the maximum concentrations ($C_{max}$), the relative appearance times ($T_{max}$), and the areas under the concentration-time curve (AUC) from zero to infinity, were calculated. These were obtained from the total of the area comprised between zero and $C_n$ ($C_n$ = last concentration found) and calculated with the trapeze method, plus the portion comprised between $C_n$ and infinity, obtained by applying the formula $C_n K_{el}$, wherein $K_{el}$ (x) is the elimination constant (=0.185) of the conventional product.

(x) The $K_{el}$ of the conventional product was calculated according to a two-compartment pharmacokinetic model (triexponential equation).

As an indication of the sustained release characteristics of the preparations, the following parameters were used: MRT (=mean residence time) and HVD (half value duration), MRT is the average residence time of the active principle in the plasma and is calculated according to the formula:

$$MRT = \frac{AUMoo}{AUCoo}$$

wherein AUMoo is the area under the first moment of the curve and AUCoo is the conventional area under the curve, both from zero to infinity.

HVD is the residence time in the plasma of an active principle equal to half of the maximum concentration: such time is calculated according to a graphic method.

Examining the results obtained from the test (see Table 1A and FIG. 2), it is noted that the delaying

TABLE 1

AVERAGE PLASMA LEVELS OF NIFEDIPINE (ng/ml) AFTER ADMINISTRATION OF THREE PREPARATIONS

| pr. | t(h) | | | | | | | | | | | |
|---|---|---|---|---|---|---|---|---|---|---|---|---|
| | 1 | 2 | 3 | 4 | 6 | 7 | 8 | 9 | 12 | 14 | 16 | 24 |
| "A" | 65.4 | 28.1 | 16.9 | 11.9 | 7.9 | 72.0 | 33.6 | 21.6 | 9.5 | 7.2 | 5.5 | 0.95 |
| "B" | 14.7 | 32.0 | 24.0 | 30.6 | 25.2 | — | — | 8.9 | 5.1 | — | — | 1.5 |
| "C" | 19.4 | 38.0 | 40.9 | 38.7 | 25.9 | — | — | 18.8 | 12.6 | — | — | 4.5 |

TABLE 2

MAIN PHARMACOKINETIC CHARACTERISTICS OF TEST PREPARATIONS

| Preparation | $C_{max}$ (ng/ml) | $T_{max}$ (h) | AUC 0-∞ (ng/ml × h) | X/A[a] (%) |
|---|---|---|---|---|
| "A" | 65.4 | 1 | 363.5 | — |
| "B" | 32.0 | 2 | 261.7 | 72.0 |
| "C" | 40.9 | 3 | 423.3 | 116.5 |

[a] relative bioavailability compared with reference product "A"

TABLE 3

PARAMETERS[a] INDICATING THE SUSTAINED RELEASE CHARACTERISTICS OF TEST PREPARATIONS

| preparation | MRT (h) | HV (ng/ml) | HVD (h) |
|---|---|---|---|
| "A" | 4.4 | 32.7 | 1.4 |
| "B" | 7.1 | 16.0 | 6.6 | product "A" for comparison (Adalat AR) presents its maximum level (48.2 ng/ml) one hour after the administration of the 20 mg dose, whilst the preparation "B" (Example 2) has a maximum concentration of 62.6 ng/ml two hours after swallowing of the 40 mg dose. Its average curve decreases more slowly than that of the product "A", so much so that at a distance of 24 hours after the beginning of the test, the plasmatic level is 11.4, as opposed to the 7.1 ng/ml presented by the comparison product after two administrations.

The AUC o-oo calculation gives a confirmation of the good bioavailability of the preparation in Example 2 which is equal to 134% with respect to that of the comparison product (see Table 2A).

Also the retard product characteristics are in favour of the preparation "B". In fact, it has a MRT of 10.5 hours, whilst that calculated for product "A" is 5.6 hours; the HVD is 7 hours for Example 2 and 3.3 hours for Adalat AR. Therefore, the residence time of nifedipine in the plasma is pratically doubled with the administration of the product "B" with respect to the values found after swallowing of "A" (see Table 3A).

It can be concluded, therefore, that the formulation indicated as "Example 2", in dosage parity with the comparison product but, differing from this, in a single administration, shows, with respect to it, an improved bioavailability and a more satisfying retard product characteristic, which permits an efficient therapeutical application with a single daily administration.

TABLE 1A

AVERAGE PLASMA LEVELS OF NIFEDIPINE (ng/ml)
AFTER ADMINISTRATION OF THREE PREPARATIONS

| pr. | t(h) | | | | | | | | | | |
|---|---|---|---|---|---|---|---|---|---|---|---|
| | 1 | 2 | 4 | 6 | 9 | 12 | 14 | 16 | 18 | 22 | 24 |
| "A" | 48.2 | 37.2 | 22.6 | 17.2 | 7.3 | 5.4 | 56 | 31.2 | 17.2 | 7.4 | 7.1 |
| "B" | 46.4 | 62.6 | 50.7 | 39.5 | 24.9 | 20.5 | — | 17.3 | — | — | 11.4 |

TABLE 2A

MAIN PHARMACOKINETIC CHARACTERISTICS OF TEST PREPARATIONS

| preparation | $C_{max}$ (ng/ml) | $T_{max}$ (h) | AUC 0-∞ (ng/ml × h) | X/A$^{(a)}$ (%) |
|---|---|---|---|---|
| "A" | 48.2 | 1 | 521.3 | — |
| "B" | 62.6 | 2 | 697.9 | 133.9 |

$^{(a)}$relative bioavailability compared with reference product "A"

TABLE 3A

PARAMETERS$^{(a)}$ INDICATING THE SUSTAINED RELEASE CHARCTERISTICS OF TEST PREPARATIONS

| Preparation | MRT (h) | HV (ng/ml) | HVD (h) |
|---|---|---|---|
| "A" | 5.6 | 24.1 | 3.3 |
| "B" | 10.5 | 31.3 | 7.0 |

$^{(a)}$MRT = mean residence time
HV = half value
HVD = half value duration

We claim:

1. A solid pharmaceutical formulation consisting essentially of nifedipine as active principle, PEG, and inert excipient, characterized in that a starting solid micronized inert excipient which is soluble in the gastrointestinal juices is provided either per se or homogeneously admixed with micronized active principle, and in that polyethylene glygol of high molecular weight between about 2000 and 6000 is precipitated thereon in the case of an admixture of the starting micronized inert excipient plus micronized active principle, or in that polyethylene glycol of high molecular weight between about 2000 and 6000 together with micronized active principle is co-precipitated on the starting micronized inert excipient per se, the product being in the form of very fine particles having an extremely high total specific surface.

2. Solid pharmaceutical formulation according to claim 1 in the form of a sustained release tablet.

3. Product according to claim 2, characterized by the fact that substances which swell upon contact with the gastrointestinal juices and succesively dissolve slowly, and which are selected from hydroxypropylmethylcellulose, methylcellulose, hydroxypropylcellulose, carboxyvinyl polymers, xanthan gum, in quantities varying in weight between 5% and 50% of the tablet, are added so as to obtain a prolongation of the retard effect.

4. Product of claim 3, wherein the percentage is between 10% and 30% by weight of the tablet.

5. Pharmaceutical formulation according to claim 1, characterized by the fact that the ratio between active principle and polyethylene glycol varies between 20:80 and 80:20.

6. Pharmaceutical formulation according to claim 1, characterized by the fact that the polyethylene glycol has a molecular weight between 5000 and 6000.

7. Pharmaceutical formulation according to claim 1, characterized by the fact that a co-precipitate is obtained in at least one phase.

8. Pharmaceutical formulation according to claim 1 in the form of a tablet, characterized by the fact that there is at least one type of hydroxypropylmethylcellulose present among the excipients.

9. Pharmaceutical formulation according to claim 1 in the form of tablets characterized by the fact of having a retard effect such that a single daily administration can be effected.

10. A form of oral administration based on nifedipine containing a solid pharmaceutical formulation as specified in claim 1.

11. Product according to claim 1, characterized by the fact that the micronized inert excipient is chosen from sucrose, lactose, glucose, fructose, levulose, mannitol, sorbitol, glycocoll, xylitol, pentaerythrite, and maltodextrine.

12. Product according to claim 1, characterized by the fact that the ratio between the propylene glycol plus active principle and the micronized inert excipient varies between 1:20 and 1:4.

13. Pharmaceutical formulation according to claim 1, characterized by the fact that the ratio between active principle and polyethylene glycol is between 40:60 and 60:40.

* * * * *

UNITED STATES PATENT AND TRADEMARK OFFICE
CERTIFICATE OF CORRECTION

PATENT NO. : 4,880,623

DATED : Nov. 14, 1989

INVENTOR(S) : Rossi Piergiorgio, Calanchi Massimo

It is certified that error appears in the above-identified patent and that said Letters Patent is hereby corrected as shown below:

Title Page, [57], Abstract, Line 3; "In" should read -- It --.

Column 1, line 21; "suspensions" should read -- suspension --.

Column 1, line 25; "pills, hard" should read -- pills, or hard --.

Column 2, line 19; "glicol" should read -- glycol --.

Column 2, line 39; "finall" should read -- finally --.

Column 3, line 65; "a inox" should read -- an inox --.

Column 4, line 9; "a inox" should read -- an inox --.

Column 4, line 53; "a inox" should read -- an inox --.

Column 5, line 14; "with" should read -- and --.

Column 5, line 27; "a inox" should read -- an inox --.

Column 5, line 47; "a inox" should read -- an inox --.

UNITED STATES PATENT AND TRADEMARK OFFICE
CERTIFICATE OF CORRECTION

PATENT NO. : 4,880,623

DATED : Nov. 14, 1989

INVENTOR(S) : Rossi Piergiorgio, Calanchi Massimo

It is certified that error appears in the above-identified patent and that said Letters Patent is hereby corrected as shown below:

Column 6, line 66; "(Exemple 1)" should read -- (Example 1) --.

Column 9, line 66; "glygol" should read -- glycol --.

Signed and Sealed this

Sixteenth Day of October, 1990

Attest:

HARRY F. MANBECK, JR.

*Attesting Officer*       *Commissioner of Patents and Trademarks*

UNITED STATES PATENT AND TRADEMARK OFFICE
CERTIFICATE OF CORRECTION

PATENT NO. : 4,880,623

DATED : Nov. 14, 1989

INVENTOR(S) : Piergiorgio Rossi, Massimo Calanchi

It is certified that error appears in the above-identified patent and that said Letters Patent is hereby corrected as shown below:

Title page under United States Patent [19]; "Piergiorgio et al." should read -- Rossi et al. --.

Title page [75] Inventors: "Rossi Piergiorgio, Milan; Calanchi Massimo," should read -- Piergiorgio Rossi, Milan; Massimo Calanchi, --.

Please change the inventors name on the Certificate of Correction issued October 16, 1990, from
"Rossi Piergiorgio, Calanchi Massimo" to -- Piergiorgio Rossi, Massimo Calanchi -- both on page 1 and page 2.

Signed and Sealed this

Twenty-fifth Day of December, 1990

Attest:

HARRY F. MANBECK, JR.

*Attesting Officer*         *Commissioner of Patents and Trademarks*